Figure 1:
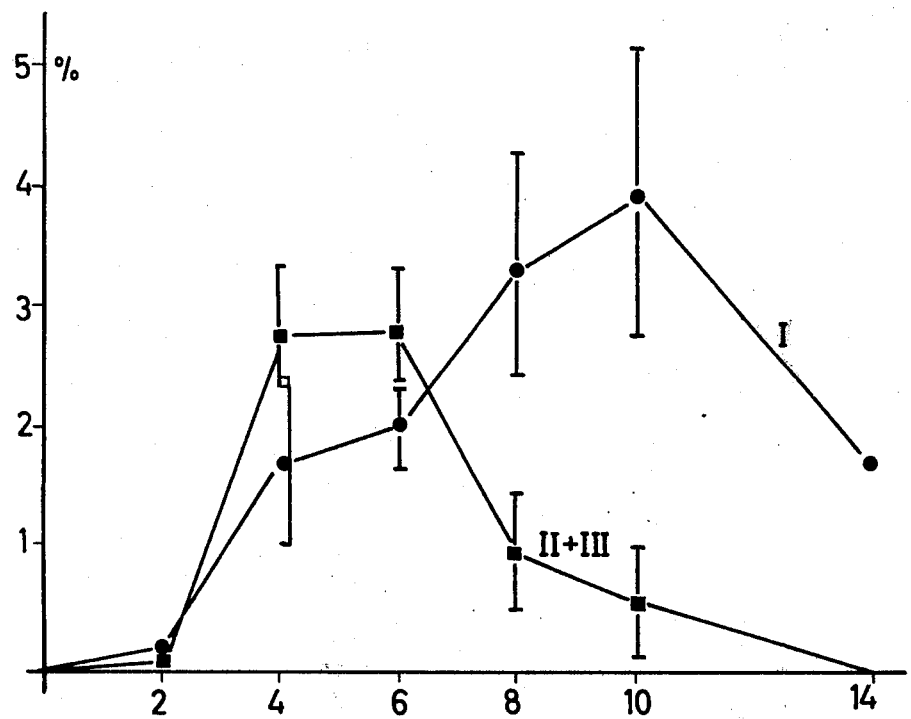

United States Patent [19]
Badicke et al.

[11] 3,978,220
[45] Aug. 31, 1976

[54] NOVEL PHENOLATE, A PROCESS FOR ITS PREPARATION AND ITS USE IN PHARMACEUTICAL COMPOSITIONS

[75] Inventors: Gerd Badicke, Opladen; Hans-Dieter Dell, Bergisch-Gladbach; Albrecht Pitzken, Bensberg-Herkenrath, all of Germany

[73] Assignee: Troponwerke Dinklage & Company, Cologne, Germany

[22] Filed: Apr. 1, 1975

[21] Appl. No.: 564,189

[30] Foreign Application Priority Data
Apr. 3, 1974 Germany............................ 2416253

[52] U.S. Cl............................. 424/267; 260/293.78
[51] Int. Cl.$^2$........................................ A61K 31/445
[58] Field of Search................. 260/293.78; 424/267

[56] References Cited
UNITED STATES PATENTS
3,280,196  10/1966  Schilling ........................ 260/611 A

OTHER PUBLICATIONS

Chemical Abstracts, 67: 98, 815a (1967) Lorenz et al.

The Merck Index, 8th Ed., Stecker et al. (Eds.) Merck & Co., Inc. (1968) pp. 390 & 752.

J. Pharmacol. Exp. Therap. 160: 243–248 (1968) Brown et al.

*Primary Examiner*—Sherman D. Winters
*Attorney, Agent, or Firm*—Burgess, Dinklage & Sprung

[57] ABSTRACT

[4-(diphenylmethoxy)-1-methylpiperidinium]-4-[1-hydroxy-2-(1-methyl-3-phenylpropylamino)-propyl]phenolate and a process for its preparation are described.

The phenolate possesses useful anti-inflammatory activity.

15 Claims, 2 Drawing Figures

NOVEL PHENOLATE, A PROCESS FOR ITS PREPARATION AND ITS USE IN PHARMACEUTICAL COMPOSITIONS

Novel phenolate, a process for its preparation and its use in pharmaceutical compositions.

This invention relates to a novel phenolate, a process for its preparation and its use in pharmaceutical compositions, in particular as antihypergicum for the treatment of excessive inflammatory reactions such as rhinitis.

It is known to use 4-(diphenylmethoxy)-1-methylpiperidine (II), known under the international abbreviated name of diphenylpyraline, as antihistamine in human medicine.

4-[1-hydroxy-2-(1-methyl-3-phenylpropylamino) propyl]phenol (III) is known under the international abbreviated name of buphenin and is used in human medicine as circulatory stimulant and vasodilator.

It is also known to use a mixture of II and III as antirhiniticum in human medicine. It has been found to be a disadvantage of using the mixture of II and III that in order to produce an optimum effect, it is necessary to prescribe a complicated dosage, the observance of which is found to be unpleasant and difficult while its non-observance, for example due to forgetfulness, jeopardises the therapeutic result. There have therefore been several attempts to find suitable Galenic preparations, for example in the form of a coated pill with delayed release, which would obviate the need for the normal hourly administration, but the individual quantities released from the preparation are subject to wide fluctuations which in some cases give rise to side effects due to temporary overdosage or result in insufficient therapeutic action.

It has now been found that these difficulties can be overcome by reacting compounds II and III to form the internal salt I of these compounds II and III and using this salt, which is less soluble in water, as the pharmaceutical composition.

This invention therefore, provides the new salt [4-(diphenylmethoxy)-1methylpiperidinium]-4-[1-hydroxy 2-(1-methyl-3-phenylpropylamino) propyl] phenolate (I).

The salt has the following chemical structural formula:

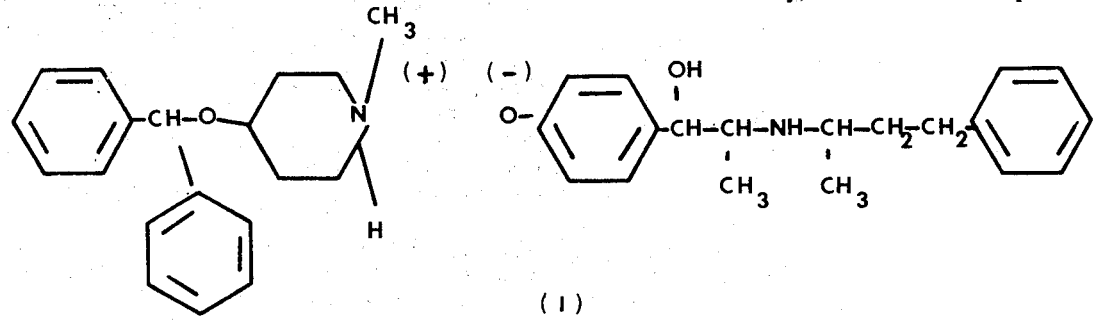

(I)

As in vitro and in vivo tests have shown, compound I hydrolyses only slowly in a neutral to alkaline medium and is therefore available longer for absorption, the active substances remain for a longer time in the organism and, as excretory tests have shown, their elimination is prolonged so that the duration of their action may also be expected to be increased.

In vitro experiments with mixtures of artificial gastric and intestinal juices have shown that, in a mixture of 50% gastric juice and 50% intestinal juice, the salt I is more than 90% hydrolysed after only 1 hour whereas, in pure intestinal juice, only 25% hydrolysis is recorded after 4 hours.

In order to obtain the optimum therapeutic activity with oral administration, it is therefore preferable and, in fact sufficient, simply to cover the salt I with a substance which is resistance to gastric juice, for example to introduce it into a capsule resistant to gastric juice.

The longer time of stay of the salt I in the body compared with gastric juice resistant preparations of the phenol III or of the mixture of the piperidine II and the phenol III can be demonstrated by excretory tests.

In the accompanying drawing the quantities of phenol III excreted as 4'-0-glucuronide after oral administration in the form of a gastric juice resistant preparation in quantities of 8.90 mg of salt I or 5 mg of a mixture of II-HCl + III-HCl are shown graphically (the quantities of active substances are molecular equivalents in both test series). It can be seen from the figure that, when the mixture is administered, maximum excretion of phenol III takes place in the second to fourth hour after ingestion whereas, after administration of salt I, maximum excretion takes place only between the eighth and tenth hour after ingestion. The elimination of the piperidine II could not be followed in these series of tests because sufficiently sensitive methods of analysis are not available.

In animal experiments it could also be shown that oral administration of the salt I has different results with regard to absorption, distribution in the organs and metabolism compared with oral administration of the mixture of II-HCl + III-HCl.

Thus after administration of salt I to the rat, the presence of the glucuronide of the phenol III could be detected in the lung, but not after administration of the mixture. The III-glucuronide content in the liver and kidney was significantly higher (up to 50%) after administration of I than after administration of III-HCl (period of investigation 1 to 16 hours).

In rabbits, the presence of intact, free phenol III in the spleen could be demonstrated after oral administration of I (1, 2 and 4 hours after application) but not after oral administration of II-HCl + III-HCl.

The free phenol III content in the liver was 19.1 $\mu$g/g weight of liver 1 hour after the application of salt I but only 2.1 $\mu$g/g 1 hour after the application of II-HCl + III-HCl.

In the kidney, the maximum free phenol III content was reached only 1 hour after administration of the mixture and amounted to 4.0 $\mu$g/g weight of kidney, but after administration of the salt I the maximum was only reached after 4 hours and amounted to 5.1 $\mu$g/g.

The total quantity of the phenol III conjugated as glucuronide in the kidney was also higher after administration of the salt I than after administration of II-HCl + III-HCl (25.9 and 9.6 $\mu$g/g after 1 hour and 4 hours compared with 9.6 and 6.4 $\mu$g/g after 1 hour and 4 hours).

The salt I is new and has not previously been described in the literature. It can be clearly distinguished from compounds II and III by its physical data. Whereas the piperidine II is an oil and the phenol III has a yield point of 110° to 112°C, the salt I melts at 86° to 88°C.

Figure 2:
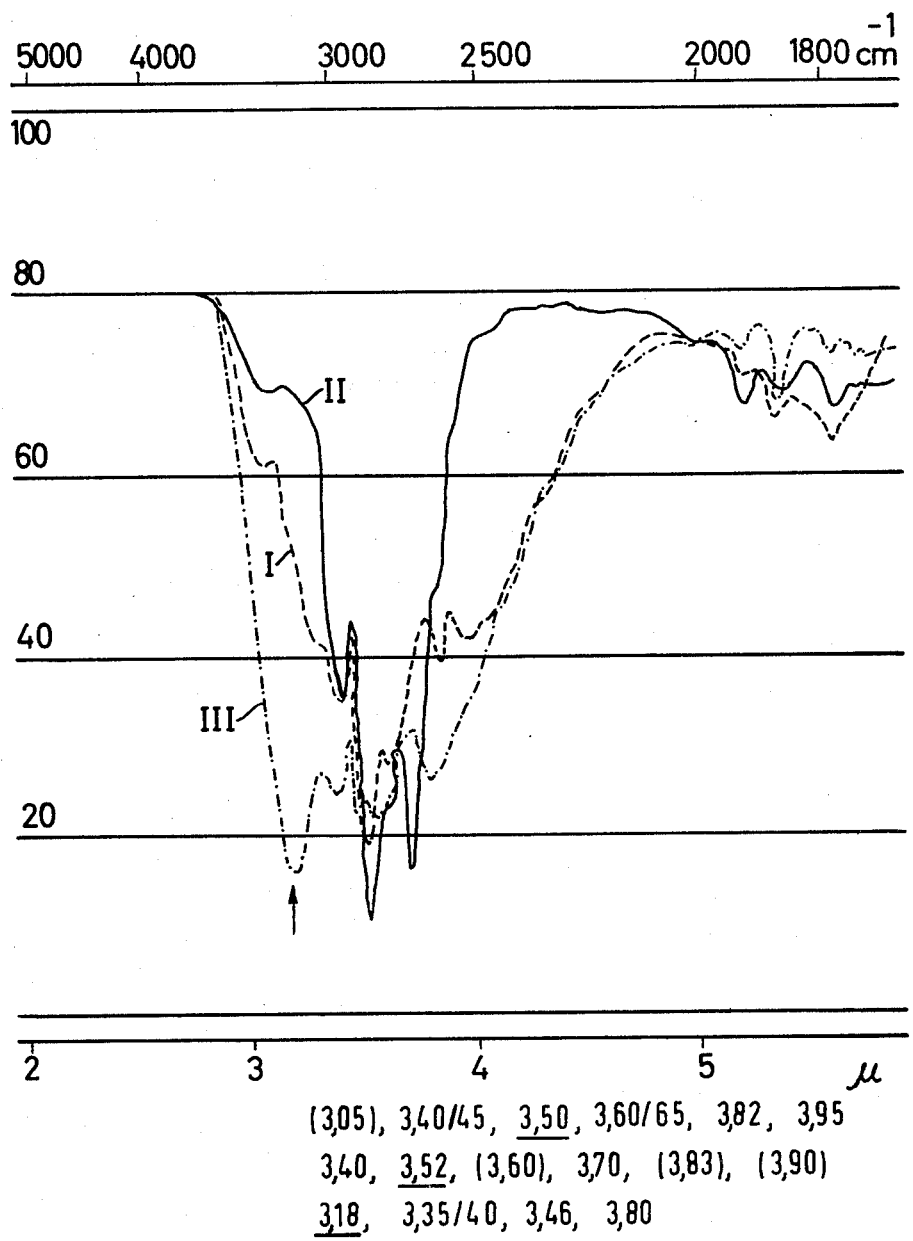

The salt I can also be clearly identified from its IR-spectrum. Whereas the phenolic OH-band appears clearly at 3.18 μ in the spectrum of the phenol III, this band has disappeared in the spectrum of the salt I and been replaced by a wide ammonium band which extends up to about 5 μ (see appended FIG. 2).

The invention also provides a process for the preparation of [4-(diphenylmethoxy)-1-methylpiperidinium]-4-[1-hydroxy-2-(1-methyl-3-phenylpropylamino)-propyl]phenolate (I), in which equimolar quantities of 4-(diphenylmethoxy)-1-methylpiperidine (II) and 4-[1-hydroxy-2-(1-methyl-3-phenylpropylamino)-propyl]phenol (III) are reacted together in known manner to form a salt. The reaction is preferably carried out by dissolving the components in a watermiscible organic solvent at elevated temperature, adding water until the solution begins to become cloudy and remains cloudy, and finally cooling. Examples of water miscible solvents include the lower alcohols, in particular methanol, ethanol, propanol and isopropanol. Temperatures up to the boiling point of the solvent used are particularly suitable for dissolving the components.

The salt I may be converted into the usual preparations for oral administration in known manner, provided that these preparations are resistant to gastric juice or can be covered with gastric juice resistant coatings. Suitable preparations of this kind include tablets, capsules, coated tablets, pills and granulates. Suppositories may be used for rectal administration. Solutions, suspensions, gels, ointments, creams or sprays may be used for local application. Auxiliary substances such as fillers, disintegrants, binders, lubricants and anti-adhesives may be incorporated in the preparations.

Suitable fillers include starch, such as corn starch, lactose or sodium chloride. The disintegrants used may be corn starch, alginic acid and alginate. Suitable binders include gelatine, polyvinyl pyrrolidone, sugar syrup, starch and size. Talcum, starch and solid polyethylene glycols may be used as lubricants. Suitable anti-adhesives include calcium and magnesium stearate, stearic acid and liquid paraffins. Hard fats and triglycerides may be used as carriers for suppositories.

The doses recommended for oral administration contain 3 to 12 mg of the salt I per dose and, in particular 5 to 7 mg of the salt I while the doses for rectal administration contain 4 to 18 mg, in particular 6 to 10 mg.

| Example for the preparation of a tablet: | |
|---|---|
| Active ingredient I | 6.0 mg |
| Corn starch | 170.5 mg |
| Talcum | 8.0 mg |
| Magnesium stearate | 4.3 mg |
| Colloidal silicon dioxide | 1.0 mg |
| Calcium carboxymethylcellulose | 2.0 mg |
| Polyvinyl pyrrolidone | 8.2 mg |
| | 200.0 mg |

The tablets are coated in known manner with a gastric juice resistant lacquer. Substances which may be used for this lacquer include, inter alia, cellulose acetate phthalate, polymers of methacrylic acid and its esters and hydroxypropyl methyl cellulose phthalate, if desired with the addition of suitable plasticisers such as castor oil, glycerol triacetate or dibutyl phthalate.

The gastric juice resistant tablets are coated in known manner with sugar syrup and/or other suitable coating suspensions, if desired with the addition of suitable dyes.

| Example for a preparation of a solution for local application: | |
|---|---|
| Active ingredient I | 100 mg |
| 30% acetic acid | 80 mg |
| Glucosemonohydrate | 5.0 mg |
| Cetrimidium bromide | 10 mg |
| Distilled water ad | 100 ml |
| Example for the preparation of suppositories | |
| Active ingredient I | 8 mg |
| Glyceric ester of saturated fatty acids | 1.825 g |
| The mass is made up into suppositories in known manner. | |
| Example for the preparation of ear drops | |
| Active ingredient I | 2.5 g |
| Anhydrous glycerine | 45.0 g |
| Propylene glycol | 50.0 g |
| Triethanolamine | 2.5 g |

Example 1

Preparation of [4-(diphenylmethoxy)-1-methyl-piperidinium]-4-[1-hydroxy-2-(1-methyl-3-phenyl-propylamino)propyl]phenolate 14.97 g of 4-[1-hydroxy-2-(1-methyl-3-phenylpropyl amino)propyl]phenol and 14.07 g of 4-(diphenylmethoxy)-1-methyl piperidine were dissolved in 300 to 500 ml of methanol at elevated temperature and heated to boiling with mechanical stirring. Water was then added dropwise under continued stirring until the cloudiness which occurred at the point where the water entered the reaction mixture no longer dissolved. The reaction solution was cooled with stirring, [4-(diphenylmethoxy)-1-methyl piperidinium]-4-[1-hydroxy-2-(1-methyl-3-phenylpropylamino) propyl]-phenolate separating in the form of colourless crystals which melted at 86° to 88°C. The yield was above 90% of the theory.

For $C_{38}H_{48}N_2O_3$ (580.82): Calculated: C, 78.58 %, H, 8.33 %, N, 4.83 %. Found: C, 78.51 %, H, 8.29 %, N, 4.84 %.

We claim:
1. [4-(diphenylmethoxy)-1-methylpiperidinium]-4-[1-hydroxy-2-(1-methyl-3-phenylpropylamino) propyl]phenolate.

2. A process for the preparation of [4-(diphenylmethoxy)-1-methylpiperidinium]-4-[1-hydroxy-2-(1-methyl-3-phenyl propylamino)propyl]phenolate which process comprises contacting in substantially equimolar quantities 4-(diphenylmethoxy)-1-methylpiperidine and 4-[1-hydroxy-2(1-methyl-3-phenylpropylamino)-propyl]phenol at a sufficiently elevated temperature to result in salt formation of the corresponding [4-(diphenylmethoxy)-1-methylpiperidinium]-4-[1-hydroxy 2-(1-methyl-3-phenylpropylamino)propyl]phenolate.

3. A process as claimed in claim 2 in which the reaction components are dissolved in a water-miscible organic solvent at elevated temperature, water is added until the solution begins to become cloudy and remains cloudy and the reaction mixture is cooled.

4. A process as claimed in claim 3 in which the water-miscible organic solvent is a lower alcohol.

5. A process as claimed in claim 4 in which the solvent is a lower alcohol selected from the group consisting of methanol, ethanol, propanol and isopropanol.

6. A process as claimed in claim 3 in which the reaction is carried out at a temperature up to the boiling point of the solvent used.

7. A pharmaceutical composition comprising as active ingredient antiphlogistically effective amounts [4-(diphenylmethoxy)-1-methylpiperidinium]-4-[1-hydroxy-2-(1-methyl-3-phenylpropylamino)propyl]-phenolate, in association with a pharmaceutical carrier.

8. A composition as claimed in claim 7 in solid form.

9. A composition as claimed in claim 8 in a form selected from the group consisting of tablet, capsule, pill and granulate form, which is coated with a gastric-juice resistant coating.

10. A composition as claimed in claim 9 in unit dosage form, each unit containing from 3 to 12 mg of active ingredient.

11. A composition as claimed in claim 10 in unit dosage form, each unit containing from 5 to 7 mg of active ingredient.

12. A composition as claimed in claim 7 in the form of a suppository for rectal administration.

13. A composition as claimed in claim 12 in unit dosage form, each unit containing from 4 to 18 mg of active ingredient.

14. A composition as claimed in claim 13 in unit dosage form, each unit containing from 6 to 10 mg of active ingredient.

15. A method of treating a patient suffering from or susceptible to an inflammatory reaction which comprises administering [4-(diphenylmethoxy)-1-methylpiperidinium]-4-[1-hydroxy-2-(1-methyl-3-phenylpropylamino)propyl]phenolate in antiphlogistically effective amounts.

* * * * *